United States Patent
Payne et al.

(10) Patent No.: US 7,971,289 B2
(45) Date of Patent: Jul. 5, 2011

(54) PORTABLE SELF-CONTAINED BED-ON-DEMAND SYSTEM

(75) Inventors: Michael Payne, Charlottesville, VA (US); Michael Carmagnola, Jr., Crozet, VA (US); Byron Scott Creasy, Charlottesville, VA (US)

(73) Assignee: Emerg, LLC, Crozet, VA (US)

( * ) Notice: Subject to any disclaimer, the term of this patent is extended or adjusted under 35 U.S.C. 154(b) by 718 days.

(21) Appl. No.: 11/851,412

(22) Filed: Sep. 7, 2007

(65) Prior Publication Data

US 2009/0064415 A1 Mar. 12, 2009

(51) Int. Cl.
*A61G 7/00* (2006.01)

(52) U.S. Cl. ............. 5/2.1; 5/53.1; 5/308; 5/284; 5/423; 5/620

(58) Field of Classification Search ............... 5/174–180, 5/111, 2.1, 53.1, 308, 284, 423; 312/258, 312/236, 209
See application file for complete search history.

(56) References Cited

U.S. PATENT DOCUMENTS

| | | | | |
|---|---|---|---|---|
| 3,514,794 A * | 6/1970 | Giancarlo | .......................... | 5/2.1 |
| 3,724,172 A * | 4/1973 | Wood | .............................. | 95/287 |
| 4,753,055 A * | 6/1988 | Durham, Jr. | ...................... | 52/28 |
| 5,653,064 A * | 8/1997 | Kappers et al. | ................ | 52/36.4 |
| 5,878,536 A * | 3/1999 | Demmitt et al. | ............... | 52/36.4 |
| 6,060,876 A * | 5/2000 | Glasband et al. | ............. | 323/355 |
| RE39,108 E * | 5/2006 | Glasband et al. | ............. | 323/355 |
| 7,114,205 B2 * | 10/2006 | Choi | .................................. | 5/114 |
| 7,137,881 B2 * | 11/2006 | Walling | ....................... | 454/251 |
| 7,148,586 B2 * | 12/2006 | Lee et al. | ........................ | 307/65 |
| 7,444,705 B2 * | 11/2008 | Chang | ............................... | 5/713 |
| 7,487,646 B2 * | 2/2009 | Matsushima et al. | ........... | 62/186 |
| 7,600,277 B2 * | 10/2009 | Heimbrock | ........................ | 5/136 |
| 2007/0251165 A1 * | 11/2007 | Kern et al. | ................... | 52/173.1 |

* cited by examiner

*Primary Examiner* — Michael Trettel

(57) ABSTRACT

A portable self-contained bed-on-demand system is presented which includes a portable collapsible self-contained storage bed and support assembly and a portable self-contained peripheral support system, or headwall, adapted to the bed that supplies medical-grade power, ventilation, and an oxygen treatment system. The bed-on-demand system duplicates, in a self-contained package usable outside a hospital environment, the critical facilities provided to a patient in a traditional hospital room.

24 Claims, 11 Drawing Sheets

PORTABLE SELF-CONTAINED BED-ON-DEMAND SYSTEM

BACKGROUND OF THE INVENTION

The present invention relates generally to emergency medical equipment, and more particularly to a bed-on-demand system which provides the key features and components of a hospital bed and headwall typically found in a standard hospital room, yet in a portable self-contained package that can be set up and used anywhere without the infrastructure of the standard hospital room.

Recent large scale disasters including natural disasters such as hurricanes, tsunamis, and earthquakes, and man-made disasters resulting from large-scale accidents, terrorist activities, and war, reiterates the importance of effective emergency relief and disaster response. Such disasters typically produce surges in numbers of people needing various levels of medical attention.

Currently, the world is unprepared to adequately respond to such disasters. Post-disaster, emergency response and disaster relief management teams are faced with several problems. First, hospitals today generally operate at near-capacity even during normal times. When faced with a surge of additional patients, most hospitals simply do not have sufficient patient facilities such as patient bed capacity to handle the additional influx of patients. In addition, the disasters that have caused the surge of patients are also often responsible for the interruption, or even destruction, of hospital infrastructure such as power, communications, etc., which may result in actually diminishing a hospital's capacity. Disasters also often occur remote to nearby hospitals, and temporary triage and treatment centers must be set up on or near the site of the disaster where standard hospital facilities such as pure sine-wave AC power required by sensitive medical equipment, and ventilation and oxygen treatment systems, are unavailable.

Increasing population densities and the trend towards more frequent and higher-intensity storm systems will only increase the need for a solution to the surge capacity problems outlined above.

SUMMARY OF THE INVENTION

Embodiments of the invention include methods and apparatuses for providing portable collapsible self-contained bed-on-demand systems.

An embodiment of the invention includes a portable self-contained bed on demand system comprising a portable bed frame, a portable mattress which lies over the bed frame in a utility configuration, and a portable self-contained bedwall adaptive to operate as a wall of the portable bed frame in the utility configuration, the bedwall comprising at least one receptacle for powering external devices, an integrated self-contained power system, the bedwall comprising a ventilation system configured to supply positive airflow for a person lying on the mattress, and an oxygen treatment system configured to supply oxygen to a person lying on the mattress, the integrated self-contained power system comprising a battery backup power source, a DC inverter, and external AC power input means, and configured to power the at least one receptacle only with true sine wave AC power.

An embodiment of the invention includes a portable self-contained modular bedwall for a bed, comprising at least one power receptacle, and a self-contained power system integrated into the first cabinet which powers the at least one receptacle with true sine wave AC power complying with medical grade equipment.

An embodiment of the invention includes portable self-contained peripheral support system for a bed, comprising at least one cabinet, at least one power receptacle, a self-contained power system integrated into the at least one cabinet which powers the at least one receptacle, and a ventilation system integrated into the at least one cabinet which is powered by the power system and which is adapted to provide positive airflow ventilation to a person on the bed.

An embodiment of the invention includes a portable bedwall for a bed, comprising a cabinet configurable into a utility configuration configured for utility and a storage configuration configured for storage and portability, the storage configuration dimensionally smaller than the utility configuration, at least one power receptacle, and a self-contained power system integrated into the cabinet which powers the at least one receptacle with true sine wave AC power complying with medical grade equipment, the self-contained power system comprising battery back-up power and external power source input means.

An embodiment of the invention includes a method for providing a portable self-contained hospital bed unit, comprising assembling a portable bed comprising a portable frame and mattress, and a portable self-contained peripheral support system comprising integrated self-contained power and ventilation into a portable self-contained package.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION

Figure 1:
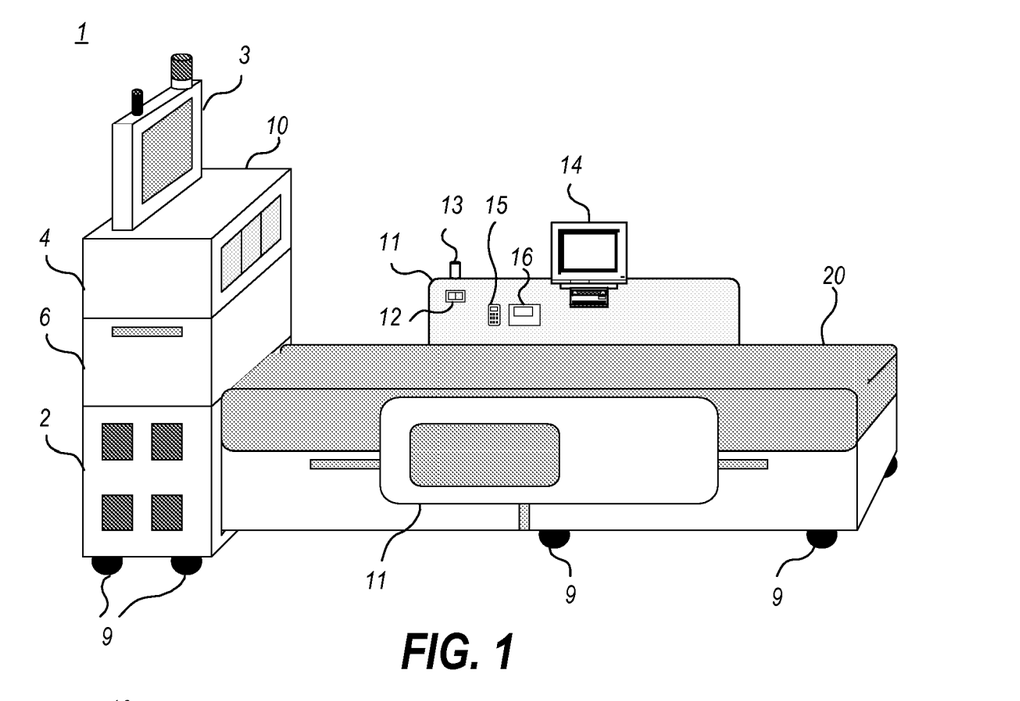
FIG. 1 is a perspective view of a portable bed-on-demand system assembled into a utility configuration.

Referring now to the drawings, there is illustrated in FIG. 1 a portable self-contained bed-on-demand system 1 including a portable self-contained peripheral support system 10 and a portable collapsible self-contained storage bed and support assembly 20. The peripheral support system 10 is adapted to the bed 20 and includes a self-contained power system 2 including a battery backup source, external AC power source input connections for allowing connection to a portable generator or other A/C power source, and a power source controller which automatically detects the available power sources, selects an external A/C source if available or the battery backup source if no external source is available, and conditions the power signal to produce pure RMS sine wave power required for sensitive medical equipment. The peripheral support system 10 may also include a ventilation system 4, an oxygen treatment system 6, and other peripherals such as a computer monitoring station 3.

The bed-on-demand system 1 may include one or more siderails 11. The side rails 11 may include powered siderail devices that are powered by the power system 2. The siderail devices may include, by way of example only and not limitation, a nurse call switch 12 and light 13 that allows a patient to signal a nurse for assistance, an entertainment system 14 such as a display or video screen, a television, a CD, DVD or MP3 player, speakers, headphone outlets, headphones, an internet connection, a keyboard, a mouse or other computer selection device, a gaming system, an independent phone system 15 such as a cellular phone and charger, lighting, and environment control panel 16 used for controlling the ventilation system.

Figure 2:
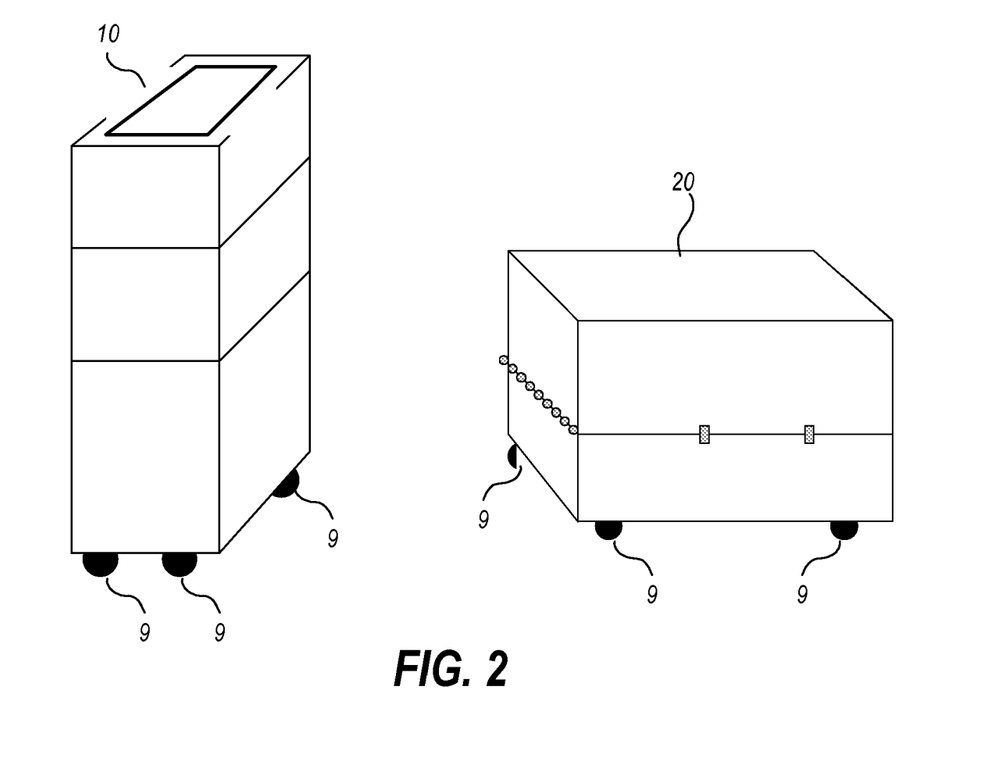
FIG. 2 is a perspective view of the portable bed-on-demand system of FIG. 1 collapsed into a storage configuration.

As illustrated in FIG. 2, both the portable self-contained peripheral support system 10 and portable bed 20 collapse into easily-portable self-contained units.

Figure 3:
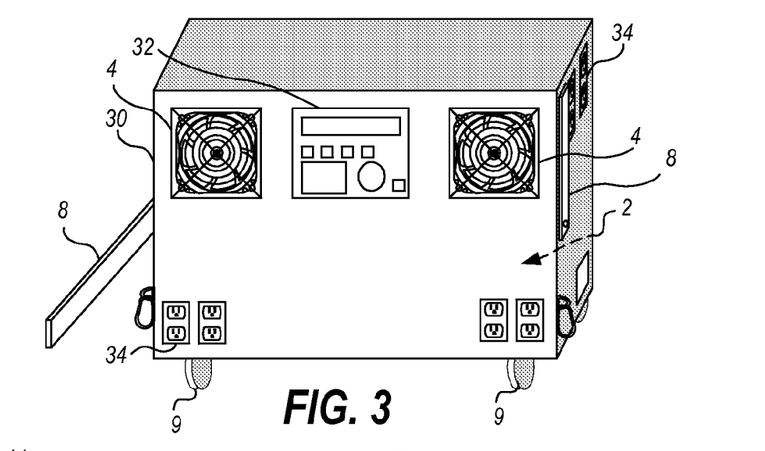
FIG. 3 is a perspective view of an embodiment of a portable self-contained peripheral support system implemented as a single modular cabinet.

In one embodiment, illustrated in FIG. 3, the portable self-contained peripheral support system 10 comprises a portable cabinet 30 with an integrated self-contained power system 2 contained therein, which is controllable by way of a power control panel 32, and which provides true sine wave AC power complying with medical grade equipment to a receptacle 34. The integrated power system 2 includes a battery backup source (not shown) and an external AC power source input 36.

The bed-on-demand peripheral support system may include an integrated ventilation system 4 powered by the power system 2 which is adapted to provide positive airflow ventilation to a person on the bed. In one embodiment, the ventilation system may be integrated into the cabinet housing the power system, as shown in FIG. 3.

Figure 4:
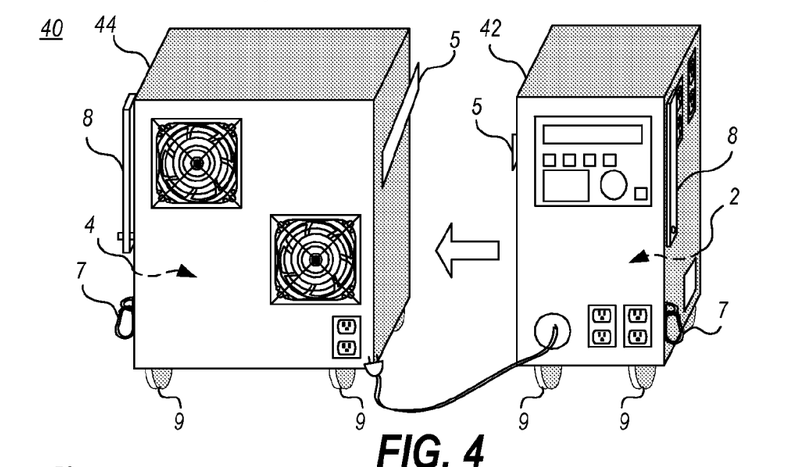
FIG. 4 is a perspective view of an embodiment of a portable self-contained peripheral support system implemented as at least two modular cabinets, including a power tower and a ventilation tower.

In another embodiment, illustrated at 40 in FIG. 4, the power system 2 is integrated into a first modular cabinet 42, which is referred to herein as the "power tower", while the positive airflow ventilation system 4 is integrated into a second modular cabinet 44, which is referred to herein as the "ventilation tower".

Figure 5:
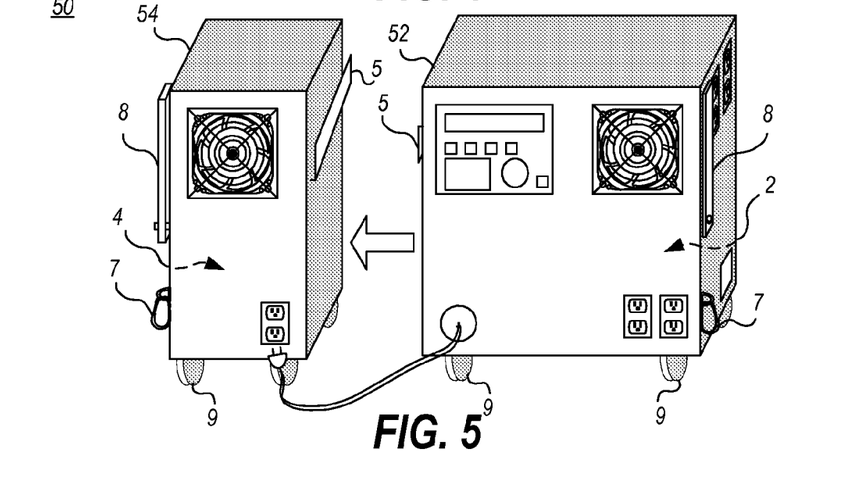
FIG. 5 is a perspective view of a power tower and ventilation tower, wherein the exhaust system is integrated into the power tower.

In another embodiment, illustrated at 50 in FIG. 5, the exhaust ventilation may be integrated into the power tower 52 to co-function as a cooling system for the power system 2, while the supply ventilation may be integrated into a separate modular ventilation tower 54 to better ensure that air heated by the power system 2 is not blown into the bed area.

The modular cabinets 42/44 and 52/54 may be attachable to one another to form a wall, such as a headwall, of the portable bed 10. In one embodiment, the modular cabinets are attached by way of fasteners 5, hooks, mating locking brackets, Velcro®, or any other connection mechanism. Furthermore, the modular cabinets need not be physically attached but may simply be aligned next to each other to form the wall of the bed, or may be positioned separately near the bed in any convenient location (for example, on either side of the bed to double as side tables).

The modular cabinets may be attachable to the bed frame of the bed so as to prevent movement of the bed and peripheral support system relative to each other. In one embodiment, the cabinets are equipped with a caribener 7, clip, snap, or other fastener which fastens to or around a member of the bed frame.

Figure 6:
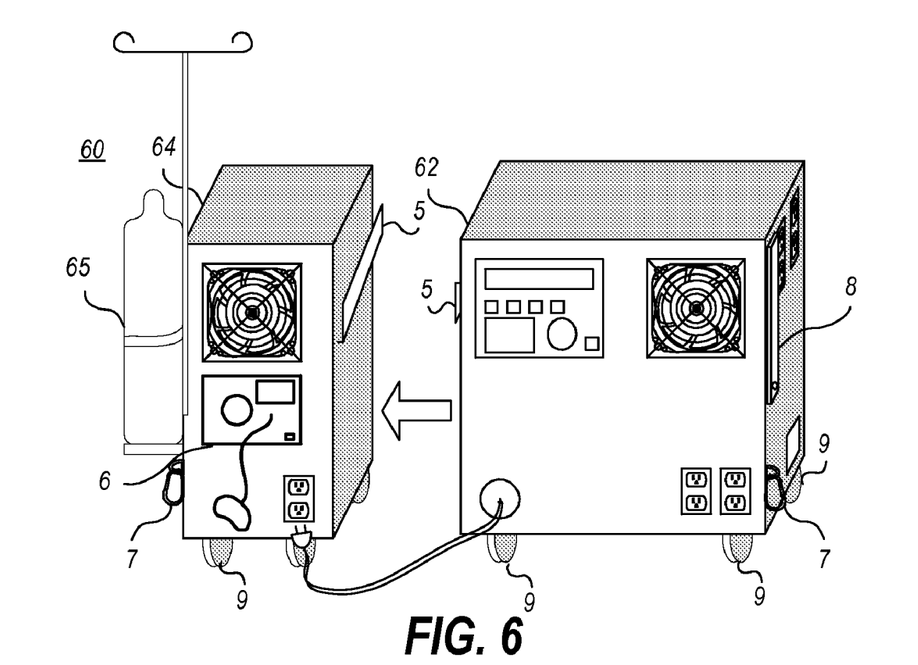
FIG. 6 is a perspective view of a power tower and ventilation tower, wherein an oxygen treatment system is integrated into the ventilation tower.

The peripheral support system may also include an oxygen treatment system 6 configurable for providing oxygen to a person on the bed. In an embodiment, the oxygen treatment system 6 includes a pressurized oxygen source, a humidifier which humidifies oxygen, and a respirator. In an embodiment, as illustrated at 60 in FIG. 6, the oxygen treatment system is integrated into the ventilation tower 64. The ventilation tower may include storage space or a rack for holding an oxygen tank 65.

Figure 7:
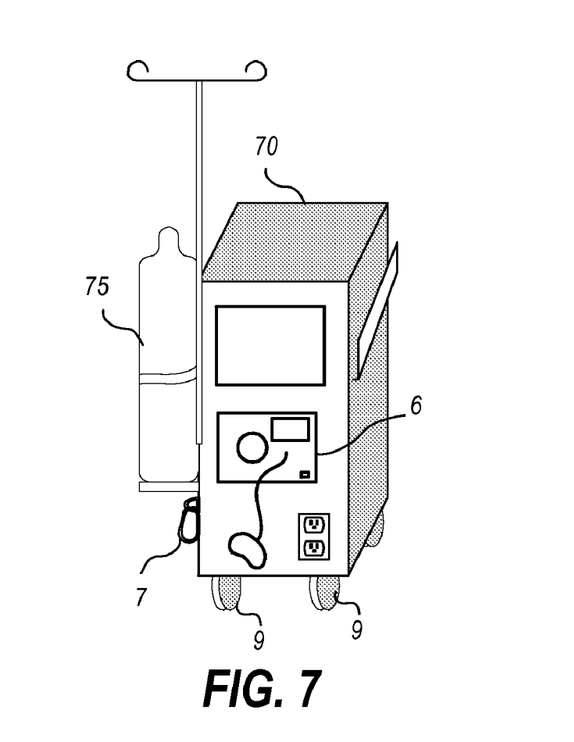
FIG. 7 is a perspective view of a modular oxygen treatment system tower that may connect to other modular components to form a peripheral support system for a bed-on-demand system.

In an alternative embodiment illustrated in FIG. 7, the oxygen treatment system 6 is integrated into a third modular cabinet 70, referred to herein as an "oxygen treatment" tower. The oxygen treatment tower may be attachable to one or both of the power tower and ventilation tower via attachment means 5. The oxygen treatment tower preferably includes storage space or a rack for holding an oxygen tank 75.

The peripheral support system 10 may also include additional modular components (for example, housing different types of medical equipment dedicated to specific functions such as a supply cabinet, monitoring equipment, a nurse station, etc.), which may be integrated into various modular cabinets dedicated to their own function, or may be integrated into one of the other modular cabinets. For example, as previously described, the ventilation system and oxygen treatment system may be integrated into a single modular cabinet or may be integrated into separate modular cabinets dedicated to their particular functions (e.g., ventilation vs. oxygen treatment). All modular components are portable, and preferably, all modular components are capable of being attached together. In an embodiment, all modular cabinets are equipped with locking wheels 9 and meet maximum weight requirements that allow two people to lift and move the cabinet. Alternatively, or in addition, the wheels 9 of the cabinet may be rubber or inflated tires that allow one person to tilt the cabinet and push, pull, and steer the cabinet in a wheelbarrow-like fashion. The cabinet may be equipped with handles or hand-holds (not shown) to allow easy gripping during transport of the cabinet.

Preferably, at least one of the modular cabinets includes storage space for storing pre-packaged emergency relief needs such as blankets, pillows, sheets, personal hygiene supplies (e.g., toothbrush and toothpaste), water bottles, and/or pre-packaged food rations.

The peripheral support system may include additional features including one or more intra-venous (IV) fluid bag stands, lighting powered by the power system, a nurse call switch/button and light, telephone capability such as a cellular phone, entertainment capability such as an audio system (e.g., speakers, CD player, MP-3 player, radio, etc.), a video system (television, DVD player, etc.), and/or a computer system which may or may not be internet-enabled.

As previously described, the peripheral support system 10 is preferably adaptable to operate as a wall (for example, a headwall as illustrated in FIG. 1) for a portable bed 20. In this capacity, at least one of the modular cabinets includes at least one siderail 8 mounted to the cabinet which collapses into a storage position for storage against or within the cabinet, and that expands from the storage position to a utility position to form a siderail for the bed. To this end, for example as shown in FIG. 3, the siderail 8 may be pivotally mounted on the cabinet 30, pivoting so that the length of the siderail is in a vertical orientation in the storage position (as illustrated on the right side of the cabinet 30 shown in FIG. 3), and pivoting so that the length of the siderail is in a horizontal orientation in the utility position (as illustrated on the left side of the cabinet 30 shown in FIG. 3). Alternatively, the siderail may be on a T-slide which slides the siderail between the storage position and the utility position. Alternatively, the siderail may be fully removable. In this case, the siderail may be stored within or, via attachment means, against the cabinet while in the storage position, and removed and attached to the cabinet (for example, by way of one or more hooks, support brackets, screws, etc.) to orient the siderail in a horizontal position along the bed to utilize the siderail.

Figure 8:
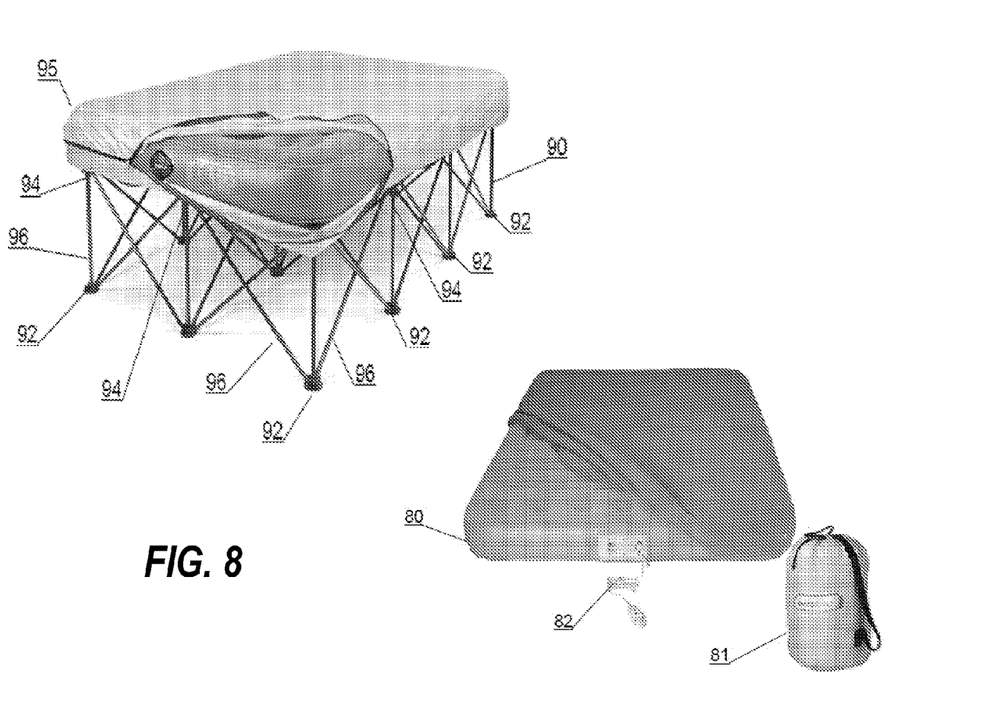
FIG. 8 is a perspective view of a bed frame compressed in an expanded configuration.
Figure 9:
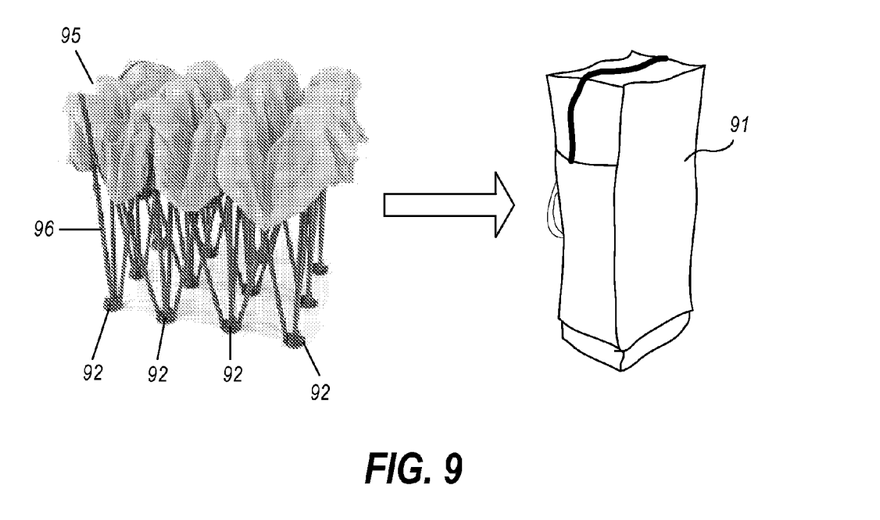
FIG. 9 is a perspective view of a mattress and bed frame in a storage configuration.

As best shown in FIGS. 8 and 9, the bed 20 includes an inflatable mattress 80 with air pump 82, and a collapsible frame 90. Referring to FIG. 8, the bed frame 90 includes a plurality of feet connectors 92 and a plurality of support connectors 94. Each foot 92 has pivotally attached thereto a plurality of frame members 96 which connect between the foot connector 92 and a plurality of nearest-neighbor support connectors 94. A nearest-neighbor support connector 94 may include a support connector opposite the foot connector 92 and/or a support connector within a shortest-distance diagonal of the foot connector 92. Each frame member 96 attached to a given foot 92 is pivotally attached to a different nearest-neighbor support connector 94. In a collapsed configuration, the frame members 96 are pivoted toward a center area, thereby compressing the feet and support connectors 92, 94 close to the center area, as illustrated in FIG. 9. In an expanded configuration, the frame members 96 are outwardly pivoted to expand the positions of the feet and support connectors 92, 94 relative to each other and away from the center area, as illustrated in FIG. 8.

The frame members 96 may be made of steel, fiberglass, aluminum, or other sturdy but preferably lightweight material. In an embodiment, the bed frame 90 includes twelve foot connectors 92 and twelve support connectors 94, and the frame members 96 are made of steel, which allows the frame to support over 300 pounds. The number of foot and support connectors 92, 94, and material with which the frame members 96 are made, may be varied to support more or less weight, or to implement different bed sizes (e.g., twin, double, or queen sizes).

As illustrated in FIG. 9, a mattress cover 95 may be attached, either permanently or through detachable fastening means such as Velcro®, snaps, buttons, etc., to the support connectors 94. The inflatable mattress 80 may be inserted within the mattress cover 95 and inflated. Upon completion of inflation, the mattress cover may be closed up, for example by way of a zipper, Velcro®, snaps, buttons, etc., to keep the air mattress securely on the frame. In an embodiment, the mattress cover 95 is made of a fabric such as nylon webbing, which is very strong but lightweight.

In one embodiment, the bed frame 80 elevates the bottom of the mattress 20" above the feet connectors, and the mattress is 9" thick, thereby elevating the patient support surface 29" off the ground surface. This assists the patient in entering and exiting the bed. It also facilitates the transport of patients between the bed and a transport stretcher and provides better ergonometric access to the patient by physicians and technicians.

In a collapsed configuration, shown best in FIG. 9, the bed frame 90 collapses for storage, and may optionally be placed in a portable bag 91. Likewise, the mattress 80 deflates and may be stored along with an air pump 82 in a portable bag 81.

Figure 10:
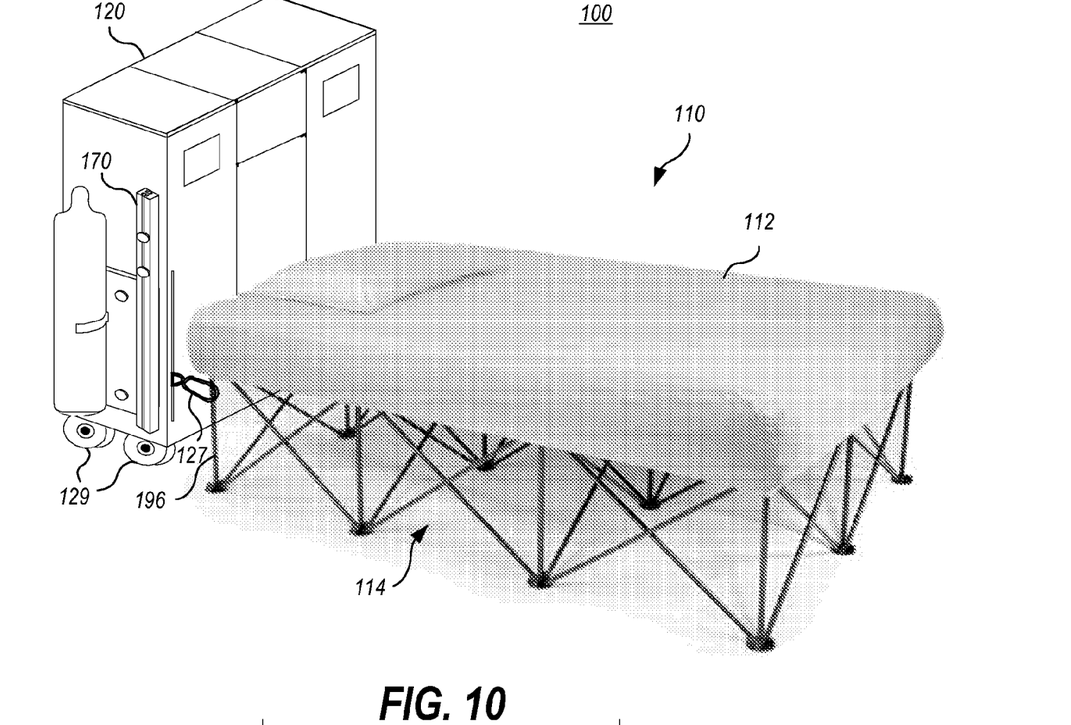
FIG. 10 is a perspective view of an exemplary embodiment of a portable bed-on-demand system assembled into a utility configuration.

Turning now to a preferred embodiment, FIG. 10 shows a bed-on-demand system 100 which includes a portable collapsible bed 110 and a collapsible bed peripheral support system 120. The bed 110 may be an inflatable mattress 112 and a collapsible frame 114, for example as described in one embodiment in FIGS. 8 and 9. The bed peripheral support system 120 is configured as a portable self-contained collapsible headwall adaptable to the portable bed 110 which provides all of the components of hospital patient bed found in a traditional hospital. In this embodiment, the bed peripheral support system 120 is referred to as the "headwall", as it is especially suitable as adapted to the head of a bed. However, it will be appreciated by those skilled in the art that the collapsible bed peripheral support system 120 may also be adapted for use at the foot of the bed, or even one of the sides of the bed to form a wall for the bed, and the term "headwall" is not intended to limit the different adaptations of the bed peripheral support system.

Figure 11:
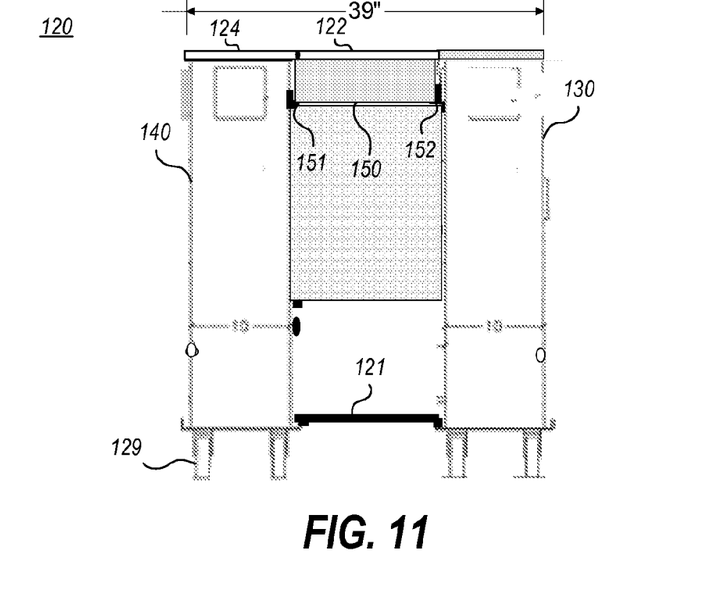
FIG. 11 is a front view of the headwall of FIG. 10 in an expanded configuration.
Figure 12:
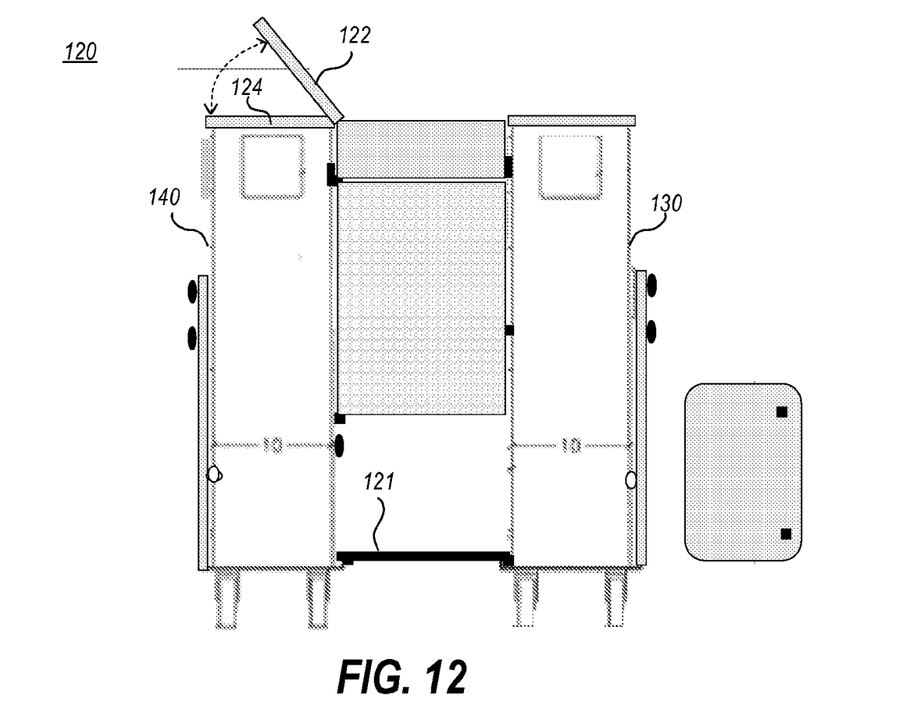
FIG. 12 is a front view of the headwall of FIG. 10 midway between an expanded configuration and a storage configuration.
Figure 13:
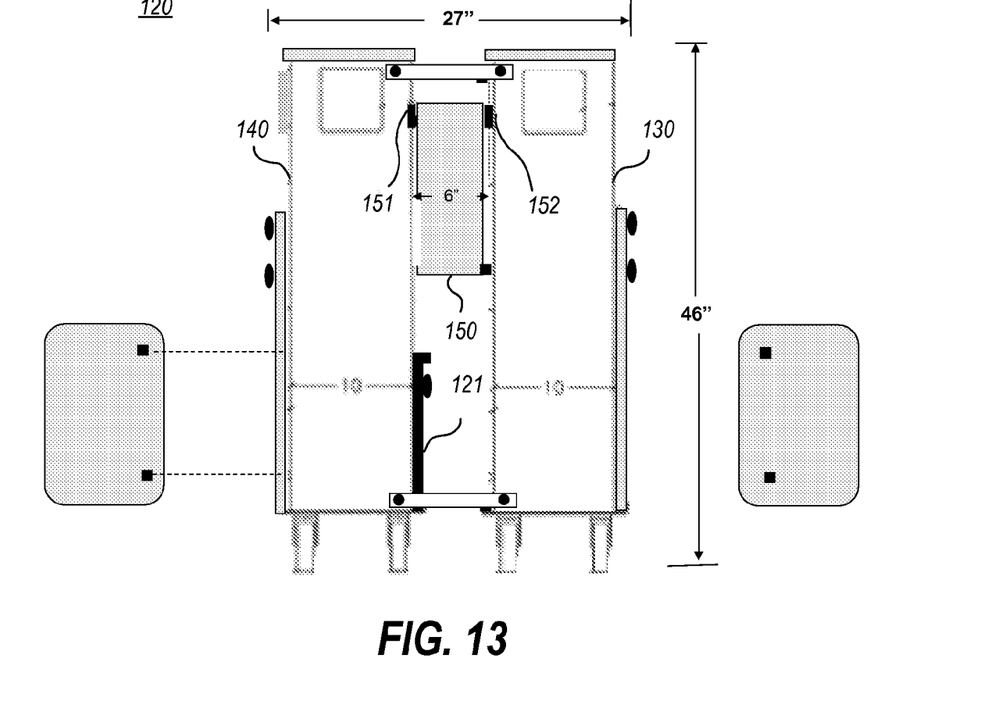
FIG. 13 is a front view of the headwall of FIG. 10 in a storage configuration.

As shown in FIGS. 10-15, the headwall 120 is configured as a modular power tower 130 connected to a modular ventilation/oxygen treatment system tower 140. The connection may be removable connection or a sliding or folding connection. In a utility configuration, the modular power tower 130 and modular ventilation/oxygen treatment system tower 140 are expanded away from each other, by way of a slide, one or more hinges, or other expandable connection means, to span the width of the bed 110. In a storage configuration, the towers 130, 140 are collapsed towards each other into a package dimensionally smaller than the utility configuration. In the illustrated embodiment, a bottom panel 121 folds down from a vertical orientation in a storage configuration (as shown in FIG. 13) to a horizontal orientation in a utility configuration (as shown in FIGS. 11 and 12), and is locked, snapped, or secured into place using any securing means. In addition, the top panel 122 of the ventilation tower 140 is hinged by way of a hinge 123 and folds toward the power tower 130 (see FIG. 12) to form a top panel over the gap between the towers 130, 140. In the storage configuration, the hinged top panel 122 is folded back over the top panel 124 of the ventilation tower 140.

As shown in FIG. 10, when expanded into the utility configuration, the headwall 120 is adapted to fit against the head of the bed 110 to form a wall. In one embodiment, the headwall 120 includes attachment means for physically attaching the bed to the headwall to prevent the bed from moving around with respect to the headwall. In an embodiment, the modular towers of the headwall include at least one caribener 127 for attachment to members 196 of the bed frame 114. The caribeners 127 may be mounted on a sliding T-slide to allow vertical and/or horizontal adjustment of the caribener to a desired position near the bed frame member 196.

The space between the two cabinets 130/140 while in the utility configuration may be maximally utilized with optional shelves or drawers 150. In one embodiment, illustrated best in FIGS. 10-12, the outer surface of the inner walls of the cabinets 130, 140 are configured with hinges 151 for folding a shelf or drawer from a vertical storage orientation (FIG. 13) to a horizontal utility configuration (FIG. 11) and supports 152 for supporting one or more shelves or drawers in the utility configuration. Shelves and/or drawers may be stored in a vertical orientation between the two cabinets when the headwall is in the storage configuration, as best shown in FIG. 13, and may be positioned in a horizontal orientation on the supports 151 between the two cabinets when the headwall is in the expanded configuration, as best shown in FIG. 11. In this embodiment, the predetermined minimum distance between the cabinets in the storage configuration must be at least as wide as the thickness of the shelves or drawers to be stored in the space.

Figure 14:
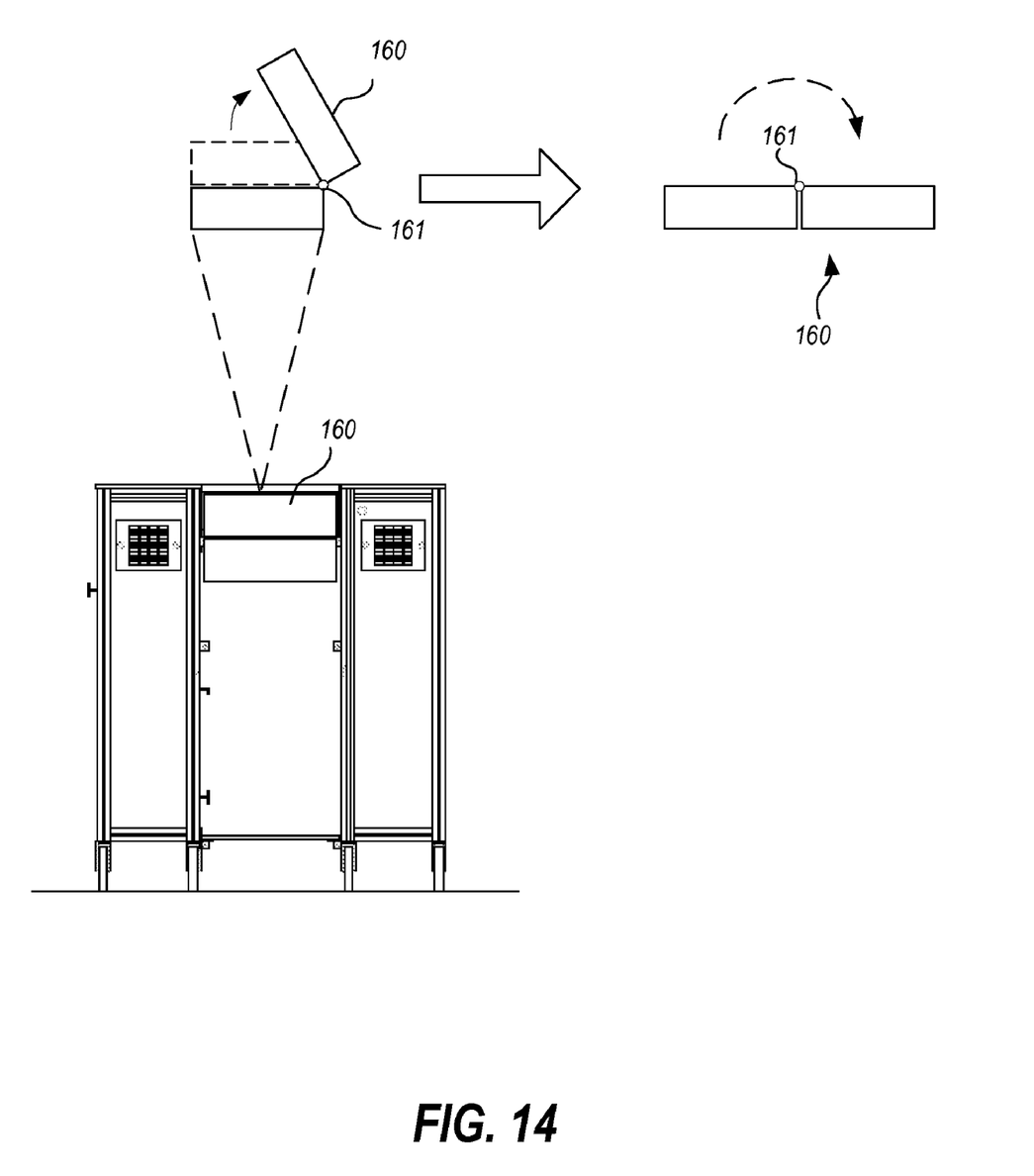
FIG. 14 is a front view of an embodiment of a folding drawer assembly for use in a portable bed-on-demand system.

Drawers may be further collapsed to minimize the distance between the cabinets in the storage configuration. For example, in one embodiment as shown in FIG. 14, a stacked set of drawers 160 may be hinged with hinge 161 along one edge so that they fold into a multi-drawer stack for the expanded configuration, and unfold to a single-drawer layer for the storage position. By unfolding the drawers to a single layer, the predetermined minimum distance between the cabinets in the storage configuration can be minimized while still allowing a maximum number of storage drawers.

Figure 15:
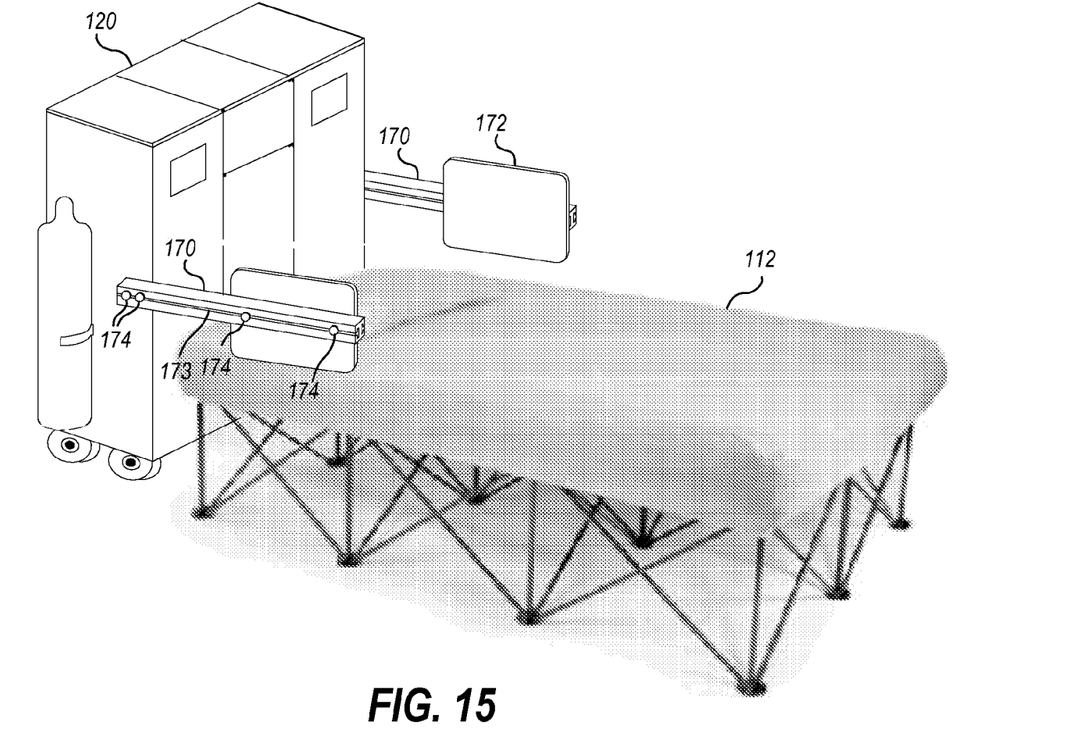
FIG. 15 is a perspective view of the bed-on-demand system of FIG. 10 with the side rails mounted.

In an embodiment, the headwall is configured with two collapsible side rails 170. Each siderail 170 is pivotally mounted on the outer sidewall of one of the cabinets 130, 140. As shown in FIG. 10, in a storage configuration, the siderail 170 is collapsed or mounted flat against the sidewall of the cabinet 130, 140 on which it is mounted such that the length of the siderail 170 is positioned in a vertical orientation. In a utility configuration, the siderail 170 is pivoted to a horizontal orientation and locked in place with a T-nut 174. When the side rails 170 are positioned in the utility configuration as illustrated in FIG. 15, the headwall 120 and side rails 170 substantially wall in the head and side of the mattress 112. The side rails 170 may be used to prevent a patient from falling out of the bed, to provide some privacy, and may include additional features that add to patient comfort.

For example, at least one of the side rails may be configured with a collapsible or removable side rail board 172 that may be used by the patient as a food tray, a writing desk, or table. In an embodiment, one siderail 170 includes a hinged table that locks into a horizontal orientation in an engaged configuration, and that collapses into or against the siderail in a storage configuration. In the embodiment shown in FIGS. 8-15, the side rails 170 are implements with Tslot rails 173 and slide-in side rail boards 172 that function as walls when mounted on the Tslot rail 173 in a vertical orientation, and which function as a table when mounted on the Tslot rail 173 in a horizontal orientation. The side rail boards 172 may be locked into the desired position using a T-nut 174. The side rail boards 172 are stored flat against the sides of the cabinets as shown in FIG. 10.

The side rails 170 may include powered siderail devices, such as those shown and discussed in relation to FIG. 1. The siderail devices may include, by way of example only and not limitation, a nurse call switch and light that allows a patient to signal a nurse for assistance, an entertainment system such as a display or video screen, a television, a CD, DVD or MP3 player, speakers, headphone outlets, headphones, an internet connection, a keyboard, a mouse or other computer selection device, a gaming system, an independent phone system such as a cellular phone and charger, lighting, and environment control panel used for controlling the ventilation system. The siderail devices may be powered by the headwall's self-contained power system.

Figure 16:
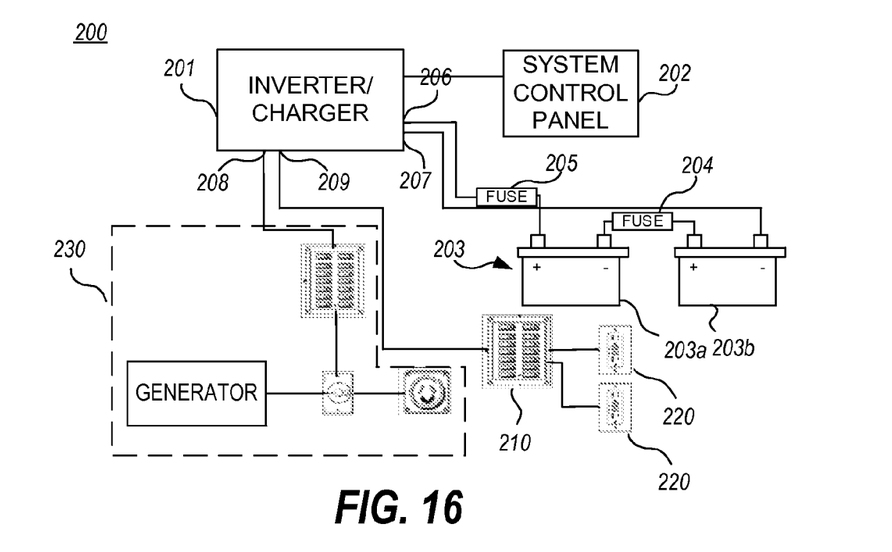
FIG. 16 is a block diagram of a power system for a portable bed-on-demand system.

Turning now in more detail to the self-contained power system 2, the power system provides uninterrupted pure sinewave AC power to at least one receptacle, and preferably multiple receptacles. In an embodiment the receptacles are implemented with a fused power strip which may include wider-spaced receptacles that allow plug-in of transformers often used to step down the power in highly-sensitive medical equipment and other electronics, in addition to standard plugs. FIG. 16 is a block diagram of an embodiment of the self-contained power system 200 that may be implemented in any of the embodiments of FIGS. 1-7 and 10-15. As illustrated, the power system 200 includes a true sine wave DC power inverter and charger 201 connected to a system control panel 202, and a DC battery source 203. The battery source 203 may be one or more batteries. In the embodiment shown, the battery source 203 includes two 12-volt rechargeable batteries 203a, 203b connected in series (by way of a fuse 204) to provide a 24-volt DC source. The inverter 201 includes DC battery hookup ports 206, 207. The positive DC port 206 is connected by way of a fuse 205 to the positive terminal of the series batteries, and the negative DC port 207 is connected to the negative terminal of the series batteries. The inverter/charger 201 also includes at least one AC input port 208 and at least one AC output port 209. The AC output port 209 is physically connected to an AC fuse panel 210, which includes fused connections to the devices of the headwall/siderail that require power. For example, the headwall may be configured with a set of ground fault interrupter circuit (GFIC) receptacles 220 which may be used to power external medical equipment. As described previously, the headwall may include additional built-in devices that require power (e.g. lighting, nurse call system, entertainment system, and the ventilation system). The AC power connections of the built-in devices may be connected to different respective fuses in the AC fuse panel 210.

The inverter/charger 201 is a smart system in that it automatically selects the AC power in 208 if available, and switches to DC 203 when the AC power is unavailable or requires conditioning due to noise or other factors. If the AC power in is not a pure sine wave, the inverter/charger 201 includes a built-in controller (not shown) which detects the "dirty" AC power (i.e., not a true sine wave due to noise or other interference on the AC input), switches the source to the DC battery 203, and connects the "dirty" AC power to charging input of the battery to recharge the battery.

External power 230 may be supplied by a building power source, a generator, or a mobile power system such as a power truck.

In a preferred embodiment, the "smart" DC power inverter/charger 201 uses true sine wave technology (rather than modified sine wave technology like most power inverters may use). A true sine wave outputs a true RMS voltage compatible with sensitive healthcare equipment rather than modified sine wave technologies that may distort, impair or fail to work correctly. In an embodiment, the "smart" DC power inverter/charger 201 is implemented using a Prosine 2.0 inverter/charger, manufactured by Xantrex Technology Inc., headquartered in Vancouver, British Columbia. The Prosine 2.0 inverter/charger provides 2000 watts of true sine wave AC power from a DC source and 100-amp multistage battery charging and combines this with a 100 amp, multistage battery charger. The "smart" inverter/charger includes an adjustable low battery cutout that prevents the battery from becoming completely discharged, a battery temperature sensor that ensures that the charge delivered to the batteries is adjusted according to their actual temperature, a multi-stage charging capability that ensures that batteries receive the "best" charge with minimal wear and tear, and a controller that detects non-pure sine wave power on the AC power source and switches seamlessly to invert mode to supply power to the receptacles with pure sine wave power derived from the batteries. When pure sine wave power is available on the AC power source, the controller switches seamlessly from deriving power from the batteries to allowing the AC source to pass through to the receptacles and to automatically begin recharging the batteries.

Figure 17:
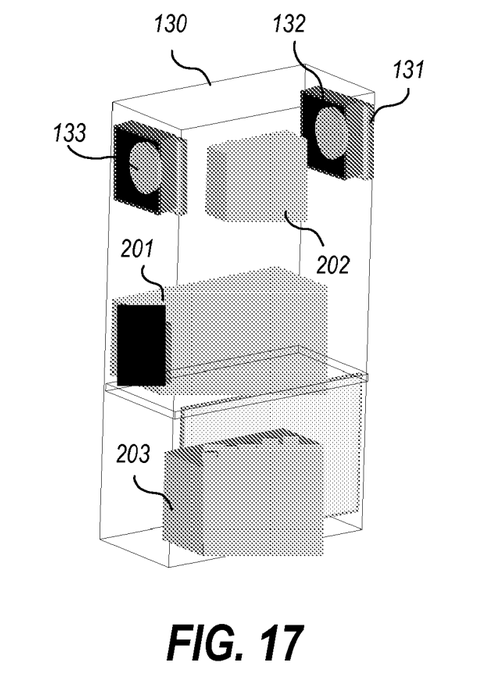
FIG. 17 is a rear perspective inside view of an exemplary embodiment of a power tower.
Figure 18:
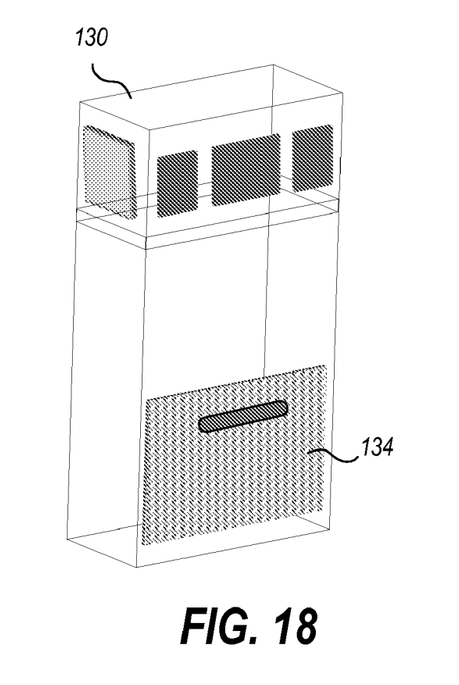
FIG. 18 is a rear perspective outside view of the power tower of FIG. 17.

FIG. 17 illustrates an example internal layout, and FIG. 18 illustrates an example outside view, of an exemplary embodiment of the power tower 130. As shown, the battery 203 is stored on a shelf and is accessible via an access panel 134. The smart DC inverter/charger 201 is stored on a second shelf, and connects to the battery. A power control panel 202 is integrated into a side of the power tower cabinet 130 to allow control of the power system, by a user, from the outside of the cabinet. The power control panel 203 connects to the inverter/charger 201. Receptacles 220 are powered by the inverter/charger 201. An air intake grill 131 and filter 132 is integrated into the cabinet panel that faces the bed. An exhaust fan 133 is integrated into the opposite panel.

Figure 19:
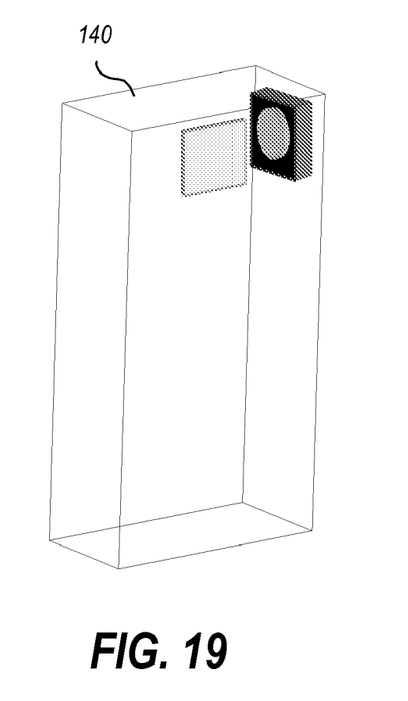
FIG. 19 is a rear perspective inside view of an exemplary embodiment of a ventilation tower.
Figure 20:
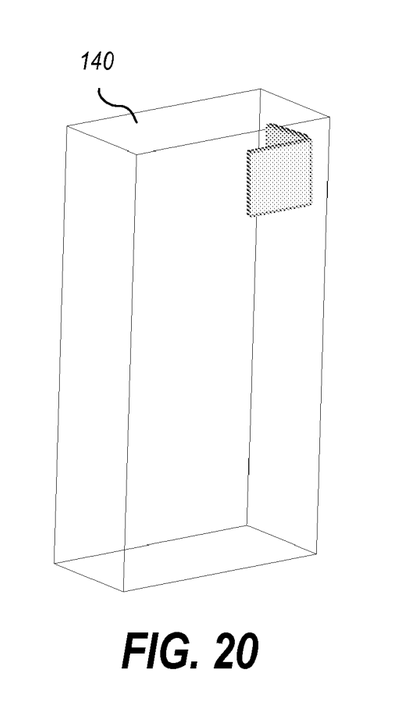
FIG. 20 is a rear perspective outside view of the ventilation tower of FIG. 19.

FIG. 19 illustrates an example internal layout, and FIG. 20 illustrates an example outside view, of an exemplary embodiment of the ventilation tower 140. As illustrated, the ventilation tower includes a supply fan with HEPA filter and grill integrated into the cabinet panel that faces the bed. The supply fan provides positive airflow in the direction of the bed for patient comfort, and an exhaust fan which provides negative airflow from the direction of the bed to maintain proper power tower and inverter temperature. Preferably, both the supply fan and exhaust fan are configured with HEPA filters to assist in air quality and contamination control. Different fans allow for positive and negative air flow control when used in the patient isolation setup. In an embodiment, the exhaust fan, filter, and associated grill assembly is integrated into the power tower to simultaneously ventilate the power system, as illustrated in FIGS. 17 and 18. In an embodiment, the supply fan is integrated into the ventilation tower away from the power system in order to prevent hot air generated by the power system from blowing onto the patient, as illustrated in FIGS. 19 and 20. Alternatively, the supply and exhaust fans may be integrated into a single cabinet or other combinations of modular cabinets.

Figure 21:
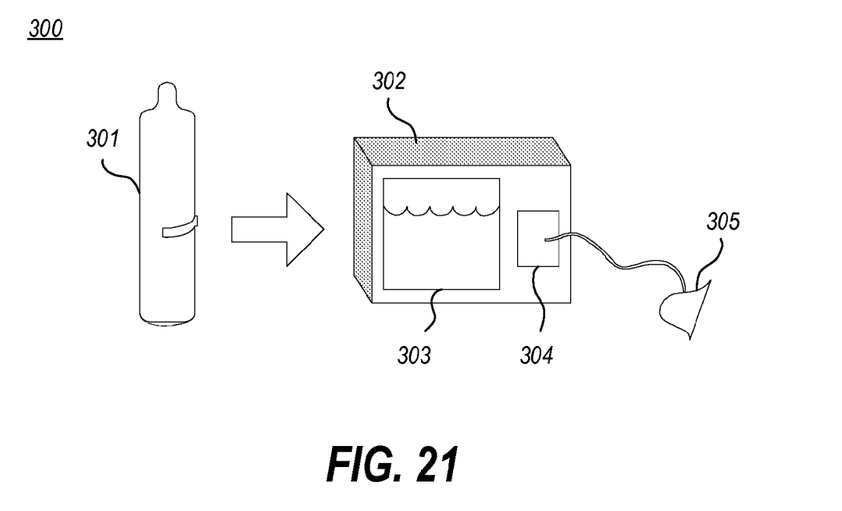
FIG. 21 is a block diagram of an oxygen treatment system.

FIG. 21 illustrates an embodiment of an oxygen treatment system 300. As illustrated, the oxygen treatment system 300 includes a source of pressurized oxygen such an oxygen tank 131, a humidifier 132 having a gas inlet which connects to the oxygen source to receive oxygen, a water reservoir 133 for storing water used to humidify the oxygen, humidifying means 134 which humidify the oxygen with the water and generates humidified oxygen at a gas-liquid outlet, and a respiratory system which includes a face mask 135 having an inlet, and one or more tubes for connecting the gas-liquid outlet of the humidifier with the inlet of the face mask. The oxygen treatment system may also include filters for the humidifier and/or face mask, a controller for controlling the oxygen delivery rate and/or humidifier temperature and humidity level. Oxygen tanks and tank holders along with all of the necessary components for setting up an oxygen treatment system are packaged.

Figure 22:
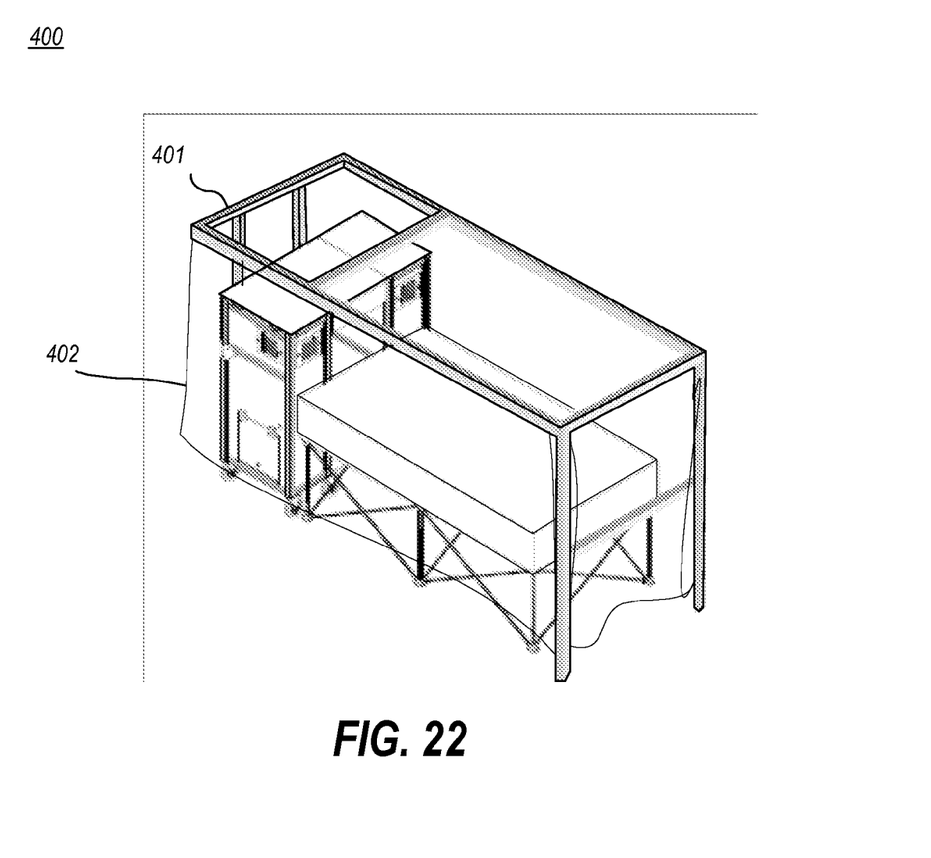
FIG. 22 is a perspective view of a portable bed-on-demand system configured with an isolation chamber.

The portable bed-on-demand system may optionally be equipped with an isolation environment, as illustrated at 400 in FIG. 22. The isolation environment 400 may include a frame 401 and a tent 402 that is secured over the frame 401. In one embodiment, the isolation environment 400 includes a plurality of poles which may be assembled into a frame 401 that fits around the headwall 120 and bed 110, and an isolation tent 402 which fits over the isolation chamber frame 401. Depending on the purpose (e.g., privacy versus environmental contamination), the isolation tent may be formed of breathable or non-breathable material, may have sides and a top, may be of various sizes and configurations to allow entering and exiting the controlled environment, and may be configured with a ventilation system between the controlled environment and the outside world. The isolation environment may be collapsible for storage in a portable modular cabinet.

A given bed-on-demand system may preferably be set up in less than ten minutes without the assistance of tools. Preferably, no tools are required for assembly.

The materials used to construct the portable bed-on-demand system are preferably lightweight but strong to ensure maximum portability without sacrificing sturdiness. In an embodiment, the modular cabinets are fabricated with TSLOTS modular structural aluminum extrusion framing system, manufactured by Futura Industries Corporation, a Delaware corporation headquartered in Clearfield, Utah. Walls of the cabinets are made of polycarbonate sheeting.

It will be appreciated from the above description that the Bed-On-Demand system duplicates, using modular self-contained portable components, all of the utilities and provisions found in a typical hospital room without requiring the hospital infrastructure. As previously described, all components of the bed-on-demand system are self-contained (requiring no outside equipment) and portable for easy storage and transport.

In one contemplated application, a large number of portable bed-on-demand systems are deployed at or near the location of an emergency and/or disaster site, where a surge of people with varying levels of medical attention need patient beds. The modular components of the bed-on-demand system are unloaded. Each bed frame/mattress assembly is expanded from its storage configuration to its utility configuration. In one embodiment, this involves expanding the bed frame from the storage configuration to the utility configuration, inserting the mattress into the mattress cover, and inflating the mattress.

The modular components of the bed peripheral support system are unloaded, and if collapsed into a storage configuration, expanded from the storage configuration into the utility configuration. Module components may be attached together to form a bedwall, which may then be attached to the bed frame (for example, by clipping the caribener(s) of the bedwall to members of the bed frame).

Side rails on the bedwall may be reconfigured from the storage configuration to the utility configuration. In one embodiment, this entails pivoting the side rails from a vertical orientation against the cabinet(s) to a horizontal orientation extending at least partially the length of the bed, and locking them into place.

The self-contained power station may be powered up via a switch on the power system control panel. The ventilation system may be turned on and/or adjusted for patient comfort, and if need be, the oxygen treatment system may be assembled for patient use and turned on.

Additional supplies such as First Aid, personnel hygiene supplies, a small quantity of food items and water, that may also be packaged and stored within modular cabinet(s) may be removed and placed in patient accessible storage such as the drawers. Sheets, blankets, and pillows, which may be packaged and stored within the modular cabinet(s) may be removed and applied to the mattress of the bed.

If the portable bed-on-demand system is equipped with an isolation environment, the isolation frame and tent are removed from the isolation environment modular cabinet, and assembled around the portable bed-on-demand system.

Figure 23:
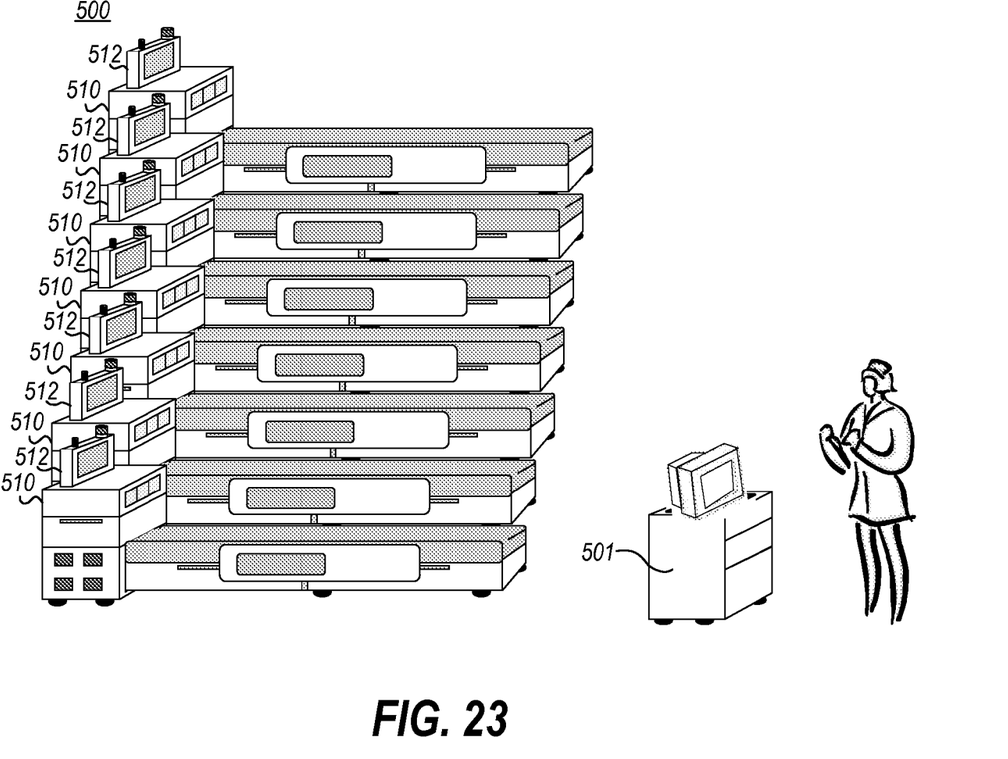
FIG. 23 is a perspective view of a plurality of bed-on-demand systems organized into a pod unit monitored by a nursing station.

A number of Bed-On-Demand systems may be organized into a unit 500, as illustrated in FIG. 23, wherein each unit 500 is monitored by a central nursing station 501 which may be packaged in its own modular cabinet. Each Bed-On-Demand 510 may be configured with a wireless LAN system 512.

A modular cabinet configured with a nursing station 501 comprising a patient monitoring system which communicates with each of the Bed-On-Demand systems 510 in the unit 500 may be set up in the unit and configured to monitor/communicate with each of the Bed-On-Demand systems in the unit via a wireless LAN system.

Figure 24:
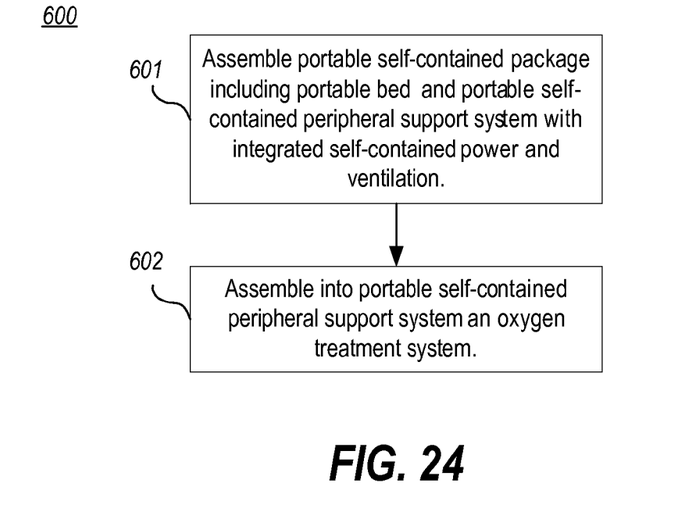
FIG. 24 is a flowchart of an exemplary embodiment of a method for providing a portable self-contained hospital bed unit.

FIG. 24 is a flowchart illustrating an exemplary embodiment 600 of a method for providing a portable self-contained hospital bed unit. As illustrated, the method includes the steps of assembling, into a portable self-contained package, a portable bed comprising a portable frame and mattress, and a portable self-contained peripheral support system comprising integrated self-contained power and ventilation (step 601). The method may further include the step of providing, in the peripheral support system, an oxygen treatment system for providing oxygen to a patient on the mattress (step 602).

As will be appreciated from the above detailed description, the portable bed-on-demand system is uniquely designed to meet the immediate needs of a hospital or disaster agency in the event of a surge of injured people with medical needs, and may be further applicable for use in airports experiencing large numbers of flight delays or cancellations, and schools or corporations having emergency closings due to weather, etc. The portable bed-on-demand system is self-contained and provides the comfort and pseudo-privacy needs of an individual over an extended amount of time.

Bed-on-demand systems may be utilized in other applications as well, including as use as a personal comfort station in airports, offices, or any environment that may generate large numbers of people on a short-term basis.

Although this preferred embodiment of the present invention has been disclosed for illustrative purposes, those skilled in the art will appreciate that various modifications, additions and substitutions are possible, without departing from the scope and spirit of the invention as disclosed in the accompanying claims.

What is claimed is:

1. A portable self-contained bed on demand system comprising:
   a portable bed frame;
   a portable mattress which lies over the bed frame in a utility configuration; and
   a portable self-contained bedwall adaptive to operate as a wall of the portable bed frame in the utility configuration, the bedwall comprising at least one receptacle for powering external devices, an integrated self-contained power system, the bedwall comprising a ventilation system configured to supply positive airflow for a person lying on the mattress, the integrated self-contained power system comprising a battery backup power source, a DC inverter, and external AC power input means, and configured to power the at least one receptacle only with true sine wave AC power.

2. The portable collapsible bed-on-demand system of claim 1, wherein at least one of the portable bed frame, portable mattress, and portable bedwall is collapsible into dimensionally smaller storage configuration.

3. The portable collapsible bed-on-demand system of claim 1, wherein the portable self-contained bedwall comprises an oxygen treatment system configured to supply oxygen to a person lying on the mattress.

4. The portable collapsible bed-on-demand system of claim 3, wherein at least one of the portable bed frame, portable mattress, and portable bedwall is collapsible into dimensionally smaller storage configuration.

5. A portable self-contained modular bedwall for a bed, comprising:
   a first modular cabinet;
   at least one power receptacle; and
   a self-contained power system integrated into the first cabinet which powers the at least one receptacle with true sine wave AC power complying with medical grade equipment; and
   a ventilation system configured to provide ventilation to a person on the bed.

6. The bedwall of claim 5, comprising:
   wherein the ventilation system is powered by the power system.

7. The bedwall of claim 5, wherein the ventilation system is integrated into a second modular cabinet which attaches to the first modular cabinet.

8. The bedwall of claim 5, comprising:
   an oxygen treatment system configurable for providing oxygen to a person on the bed.

9. The bedwall of claim 8, wherein the oxygen treatment system is integrated into a second modular cabinet which attaches to the first modular cabinet.

10. The bedwall of claim 8, comprising:
    storage for holding an oxygen tank.

11. The headwall of claim 5, comprising:
    at least one intra-venous (IV) bag stand.

12. The bedwall of claim 5, comprising:
    at least one siderail mounted to the cabinet which collapses into a storage position for storage against or in the cabinet, and that expands from the storage position to a utility position to form a siderail for the bed.

13. The bedwall of claim 12, wherein at least one siderail comprises a tray positionable in a utility position which extends over a mattress of the bed to provide a table for a patient lying in the bed, and positionable in a storage position wherein the tray is stored in or against the siderail and away from the bed.

14. The bedwall of claim 12, wherein at least one siderail comprises an electronic device which is powered by the integrated power system of the bedwall.

15. The bedwall of claim 5, the bedwall configurable into a utility configuration configured for use by a patient and a storage configuration configured for storage and portability, the storage configuration dimensionally smaller than the utility configuration.

16. A portable self-contained peripheral support system for a bed, comprising:
- at least one cabinet;
- at least one power receptacle;
- a self-contained power system integrated into the at least one cabinet which powers the at least one receptacle; and
- a ventilation system integrated into the at least one cabinet which is powered by the power system and which is adapted to provide positive airflow ventilation to a person on the bed.

17. The peripheral support system of claim 16, wherein the receptacle provides true sine wave AC power complying with medical grade equipment.

18. A portable bedwall for a bed, comprising:
- a cabinet configurable into a utility configuration configured for utility and a storage configuration configured for storage and portability, the storage configuration dimensionally smaller than the utility configuration;
- at least one power receptacle; and
- a self-contained power system integrated into the cabinet which powers the at least one receptacle with true sine wave AC power complying with medical grade equipment, the self-contained power system comprising battery back-up power and external power source input means.

19. The portable bedwall of claim 18, comprising:
- at least one drawer or shelf which is positioned in the cabinet in a horizontal orientation when the cabinet is in the utility configuration, and which is repositioned in the cabinet in a vertical orientation when the cabinet is in the storage configuration.

20. The portable bedwall of claim 18, comprising:
- a folding drawer unit which folds into a drawer stack and is insertable in the cabinet in a horizontal orientation when the cabinet is in the utility configuration, and which unfolds into a single layer and is stored in a vertical orientation in the cabinet when the cabinet is in the storage configuration.

21. The bedwall of claim 18, wherein the bedwall is adapted to operate as a wall for a bed, the bedwall further comprising at least one siderail mounted to the cabinet which collapses into a storage position for storage against or in the cabinet, and that expands from the storage position to a utility position to form a siderail for the bed.

22. The bedwall of claim 21, wherein at least one siderail comprises a tray positionable in a utility position to form a table surface usable by a person in the bed, and positionable in a storage position wherein the tray is stored in or against the siderail.

23. The bedwall of claim 21, wherein at least one siderail comprises an electronic device which is powered by the integrated power system of the bedwall.

24. A method for providing a portable self-contained hospital bed unit, the method comprising:
- assembling a portable bed comprising a portable frame and mattress, and a portable self-contained peripheral support system comprising integrated self-contained true sine wave AC power complying with medical grade equipment and ventilation, and an oxygen treatment system for providing oxygen to a patient on the mattress, into a portable self-contained package.

* * * * *